(12) United States Patent
Grueebler et al.

(10) Patent No.: US 10,987,119 B2
(45) Date of Patent: Apr. 27, 2021

(54) SURGICAL INSTRUMENT HAVING A SURFACE TEXTURE

(71) Applicant: Novartis AG, Basel (CH)

(72) Inventors: Reto Grueebler, Greifensee (CH); Markus Hupp, Zurich (CH); Pooria Sharif Kashani, Irvine, CA (US)

(73) Assignee: Alcon Inc., Fribourg (CH)

( * ) Notice: Subject to any disclaimer, the term of this patent is extended or adjusted under 35 U.S.C. 154(b) by 297 days.

(21) Appl. No.: 15/708,630

(22) Filed: Sep. 19, 2017

(65) Prior Publication Data

US 2018/0103972 A1    Apr. 19, 2018

Related U.S. Application Data

(60) Provisional application No. 62/517,504, filed on Jun. 9, 2017, provisional application No. 62/409,660, filed on Oct. 18, 2016.

(51) Int. Cl.
| | |
|---|---|
| *A61B 17/28* | (2006.01) |
| *A61B 17/30* | (2006.01) |
| *A61B 17/29* | (2006.01) |
| *A61B 17/00* | (2006.01) |

(52) U.S. Cl.
CPC ............ *A61B 17/282* (2013.01); *A61B 17/30* (2013.01); *A61B 2017/00526* (2013.01); *A61B 2017/00982* (2013.01); *A61B 2017/2926* (2013.01)

(58) Field of Classification Search
CPC .................. A61B 17/282; A61B 17/30; A61B 2017/00526; A61B 2017/00982; A61B 2017/2926; A61F 9/00736; A61F 9/00727; A61F 9/00709; A61F 9/00718; A61F 9/007; A61F 9/00754; A61F 9/00772

See application file for complete search history.

(56) References Cited

U.S. PATENT DOCUMENTS

| | | |
|---|---|---|
| 2,795,225 A | 6/1957 | Sovatkin et al. |
| 4,671,283 A | 6/1987 | Hoskin et al. |
| 4,693,246 A | 9/1987 | Reimels |

(Continued)

FOREIGN PATENT DOCUMENTS

| | | |
|---|---|---|
| CA | 2825008 A1 | 7/2012 |
| CN | 10637419 A | 2/2010 |

(Continued)

OTHER PUBLICATIONS

Gruber, A.E., et al. "Miniaturisierte Instrumente aus Nickel-Titan Legierungen fur die minimal Invasive Therapie [Miniaturized Instruments made from Nickel-Titanium Alloys for Minimally Invasive Therapy]" Karsruhe Research vol. 32 (2000): 70-76 Published 2000.

(Continued)

*Primary Examiner* — Mohamed G Gabr

(57) ABSTRACT

Surgical instruments and, particularly, ophthalmic surgical instruments are disclosed. Example surgical instruments include forceps for removal of an internal limiting membrane (ILM). The example forceps may include a textured surface formed at a distal end of the forceps jaws. The textured surface may have a plurality of microposts that operate to increase a coefficient of friction between the ILM and the forceps in order to reduce a normal force, applied by the forceps, needed to engage the ILM.

5 Claims, 6 Drawing Sheets

(56) References Cited

U.S. PATENT DOCUMENTS

| | | |
|---|---|---|
| 4,994,079 A | 2/1991 | Genese et al. |
| 5,078,716 A | 1/1992 | Doll |
| 5,208,111 A | 5/1993 | Decher et al. |
| 5,222,973 A | 6/1993 | Shame et al. |
| 5,234,458 A | 8/1993 | Metais |
| 5,340,354 A | 8/1994 | Anderson et al. |
| 5,496,330 A | 3/1996 | Bates et al. |
| 5,601,572 A | 2/1997 | Middleman et al. |
| 5,634,918 A | 6/1997 | Richards |
| 5,700,559 A | 12/1997 | Sheu et al. |
| 5,739,237 A | 4/1998 | Russell et al. |
| 5,792,145 A | 8/1998 | Bates et al. |
| 5,810,881 A | 9/1998 | Hoskin et al. |
| 5,855,586 A | 1/1999 | Habara et al. |
| 5,919,202 A | 7/1999 | Yoon |
| 5,921,998 A | 7/1999 | Tano et al. |
| 5,972,021 A | 10/1999 | Huttner et al. |
| 6,077,274 A | 6/2000 | Ouchi et al. |
| 6,120,518 A | 9/2000 | Mark et al. |
| 6,267,759 B1 | 7/2001 | Quick |
| 6,340,354 B1 | 1/2002 | Rambin |
| D456,077 S | 4/2002 | Etter et al. |
| 6,451,037 B1 | 9/2002 | Chandrasekaran et al. |
| 6,464,629 B1 | 10/2002 | Boone et al. |
| 6,488,695 B1 | 12/2002 | Hickingbotham |
| 6,575,989 B1 | 6/2003 | Scheller et al. |
| 6,592,600 B1 | 7/2003 | Nicolo |
| 6,685,725 B2 | 2/2004 | Attinger et al. |
| 6,730,076 B2 | 5/2004 | Hickingbotham |
| 6,772,765 B2 | 8/2004 | Scheller et al. |
| 6,920,965 B2 | 7/2005 | Burgdorf et al. |
| 6,995,336 B2 | 2/2006 | Hunt et al. |
| 7,251,893 B2 | 8/2007 | Cohen et al. |
| 7,335,271 B2 | 2/2008 | Autumn |
| 7,410,606 B2 | 8/2008 | Appleby et al. |
| 7,582,327 B2 | 9/2009 | Qiu et al. |
| 7,867,230 B2 | 1/2011 | Asahara et al. |
| 7,893,413 B1 | 2/2011 | Appleby et al. |
| 8,150,506 B2 | 4/2012 | Kaushal et al. |
| 8,241,321 B2 | 8/2012 | Scheller et al. |
| 8,425,596 B2 | 4/2013 | Britton et al. |
| 8,469,993 B2 | 6/2013 | Rothberg et al. |
| 8,579,887 B2 | 11/2013 | Hanlon et al. |
| 8,795,196 B2 | 8/2014 | Cho et al. |
| 8,821,444 B2 | 9/2014 | Scheller et al. |
| 9,060,842 B2 | 6/2015 | Karp et al. |
| 9,138,346 B2 | 9/2015 | Scheller et al. |
| 9,173,772 B1 | 11/2015 | Scheller et al. |
| 9,174,184 B2 | 11/2015 | Kang et al. |
| 9,204,995 B2 | 12/2015 | Scheller et al. |
| 9,226,762 B2 | 1/2016 | Scheller et al. |
| 9,247,951 B1 | 2/2016 | Scheller et al. |
| 9,320,534 B2 | 4/2016 | Vezzu |
| 9,428,254 B1 | 8/2016 | Scheller et al. |
| 9,586,044 B2 | 3/2017 | Ross |
| 9,592,074 B2 | 3/2017 | Hanlon et al. |
| 9,629,645 B2 | 4/2017 | Scheller et al. |
| 9,775,943 B2 | 4/2017 | Scheller et al. |
| 9,795,506 B2 | 10/2017 | Scheller et al. |
| 10,039,565 B2 | 8/2018 | Vezzu |
| 2002/0068954 A1 | 6/2002 | Foster |
| 2003/0060812 A1 | 3/2003 | Hickingbotham |
| 2004/0020015 A1 | 2/2004 | Yokemura et al. |
| 2004/0193214 A1 | 9/2004 | Scheller |
| 2004/0260337 A1 | 12/2004 | Freed |
| 2007/0043352 A1 | 2/2007 | Garrison et al. |
| 2007/0179512 A1 | 8/2007 | Olsen et al. |
| 2007/0225785 A1 | 9/2007 | Park et al. |
| 2007/0239202 A1 | 10/2007 | Rodriguez |
| 2007/0282348 A1 | 12/2007 | Lumpkin |
| 2008/0021399 A1 | 1/2008 | Spaide |
| 2008/0058761 A1 | 3/2008 | Spaide |
| 2008/0167576 A1 | 7/2008 | Cho et al. |
| 2008/0183199 A1 | 7/2008 | Attinger |
| 2009/0030448 A1 | 1/2009 | Andre |
| 2010/0226943 A1 | 9/2010 | Brennan et al. |
| 2011/0015669 A1 | 1/2011 | Corcosteugi |
| 2011/0021965 A1 | 1/2011 | Karp et al. |
| 2011/0270221 A1 | 11/2011 | Ross |
| 2011/0282190 A1 | 11/2011 | Caffey et al. |
| 2013/0059113 A1 | 3/2013 | Hatton et al. |
| 2013/0204245 A1 | 8/2013 | Ivanisevic et al. |
| 2014/0135820 A1 | 5/2014 | Schaller et al. |
| 2014/0172010 A1 | 6/2014 | Vezzu |
| 2014/0277110 A1* | 9/2014 | Scheller ............... A61B 17/30 606/207 |
| 2014/0379024 A1 | 12/2014 | Schaller et al. |
| 2015/0088193 A1 | 3/2015 | Scheller et al. |
| 2015/0238355 A1* | 8/2015 | Vezzu ............... A61F 9/00736 606/207 |
| 2015/0297278 A1 | 10/2015 | Scheller |
| 2016/0066940 A1 | 3/2016 | Scheller et al. |
| 2016/0074219 A1 | 3/2016 | Scheller et al. |
| 2016/0296246 A1 | 10/2016 | Schaller |
| 2017/0119419 A1 | 5/2017 | Scheller et al. |
| 2017/0165109 A1 | 6/2017 | Gunn |
| 2017/0296382 A1 | 10/2017 | Mukai |
| 2019/0000670 A1 | 1/2019 | Grueebler |

FOREIGN PATENT DOCUMENTS

| | | |
|---|---|---|
| CN | 201624872 U | 11/2010 |
| CN | 102565057 A | 7/2012 |
| CN | 104837444 A | 8/2015 |
| CN | 104994793 A | 10/2015 |
| CN | 204839914 U | 12/2015 |
| DE | 29714735 U1 | 10/1997 |
| DE | 102009033015 A1 | 1/2011 |
| EP | 1406536 A2 | 1/2003 |
| EP | 1295580 A1 | 3/2003 |
| EP | 1511433 A1 | 3/2005 |
| EP | 1463455 B1 | 8/2005 |
| EP | 1986581 B1 | 3/2012 |
| EP | 2214590 B1 | 8/2016 |
| GB | 2086792 A | 5/1982 |
| GB | 2086792 B | 8/2018 |
| JP | S57110238 A | 7/1982 |
| JP | 2003159270 A | 6/2003 |
| JP | 2005529678 A | 10/2005 |
| JP | 2006527633 A | 12/2006 |
| RU | 43173 U1 | 1/2005 |
| SU | 117617 A1 | 11/1958 |
| WO | 199511629 | 5/1995 |
| WO | 9924091 A1 | 5/1999 |
| WO | 2003105705 A1 | 12/2003 |
| WO | 2004020015 A1 | 3/2004 |
| WO | 2005086772 A2 | 9/2005 |
| WO | 2007103671 A3 | 9/2007 |
| WO | 2008011225 A2 | 1/2008 |
| WO | 2009067649 A2 | 5/2009 |
| WO | 2011097578 A1 | 8/2011 |
| WO | 201197578 A2 | 11/2011 |
| WO | 2011143388 A2 | 11/2011 |
| WO | 2012064361 A1 | 5/2012 |
| WO | 2014078049 | 5/2014 |
| WO | 2014092956 A1 | 6/2014 |
| WO | WO2015124467 A1 | 5/2015 |
| WO | 2016063707 | 4/2016 |

OTHER PUBLICATIONS

Semeraro, Francesco, et al. "Current Trends about Inner Limiting Membrane Peeling in Surgery for Epiretinal Membranes." Journal of Ophthalmology. vol. 2015 (2015), 13 pages.
Bhisitkul, R.B., Development of Microelectromechanical Systems (MEMS) Forceps for Intraocular Surgery, C.G. Keller, Br. J. Ophthalmol, 2005; 89 pages 1586-1588. Aug. 1, 2005 (3 pages).
A Wafer-Based, 3-D Metal Micro-Manufacturing Technology for Ultraminiaturized Medical Devices Pamphlet, Oct. 29, 2008 (38 pages).
Research: Micro-Scale Surgical Tools_LIBNA, 2003 (2 pages).
Aoki, I, Takahashi, T., Mihara, S., Yamagata, Y., Higuchi, T., Trial

(56) References Cited

OTHER PUBLICATIONS

Production of Medical Micro-Tool by Metal Deformation Processes Using Moulds, 344-349. Conference date Jan. 29-Feb. 2, 1995 (6 pages).
Bhisitkul, R.B., Development of Microelectromechanical Systems (MEMS) Forceps for Intraocular Surgery, C.G. Keller, Br. J. Ophthalmol, 2005; 89: pp. 1586-1588.
"Grieshaber Revolution DSP", Alcon, Vitreoretical Product Catalog, 6 pgs., 2012 Novartis 7/12 VIT12052MSA.
Pavoor, P., Wear Reduction of Orthopaedic Bearing Surfaces Using Polyelectrolyte Multilayer Nanocoatings, Elsevier, 2006, pp. 1527-1533.
PCT/EP2015/052791; International Searching Authority, International Search Report, Apr. 24, 2015, 5 pgs.
Prosecution History, U.S. Appl. No. 14/550,470, 42 pages, Jan. 6, 2015. (5016).
Rabinovich, et al, "Adhesion between Nanoscale Rough Surfaces II. Measurement and Comparison with Theory", J.Colloid & Interface Sci., Aug. 2000, 232, pp. 17-24 (DOI:10.1006/jcis.2000.7168).
Rabinovich, et al, "Adhesion between Nanoscale Rough Surfaces, I. Role of Asperity Geometry", J.Colloid & Interface Sci., Aug. 2000, 232, pp. 10-16 (DOI:10.1006/jcis.2000.7167).
United States Patent and Trademark Office, U.S. Appl. No. 61/302,064, filed Feb. 5, 2010, pp. 1-41.
United States Patent and Trademark Office, U.S. Appl. No. 61/389,573, filed Oct. 4, 2010, pp. 1-37.
Valentin-Rodriguez, et al, "Quantitative Analysis of Human Internal Limiting Membrane Extracted from Patient with Macular Holes", Langmuir, Jun. 2010, 26(15), pp. 12810-12816 (DOI: 10.102/Ia101797e).
Valentin-Rodriguez, C., Turning the Adhesion of Layer-by-Layer Films to the Physicochemical Properties of Inner Limiting Membranes Using Nanoparticles, Elsevier, 2011, pp. 616-624.
Alexander Vankov et al., Electro-adhesive Forceps for Tissue Manipulation, Department of Ophthalmology, School of Medicine, Stanford Univ.
Celimar Valentine-Rodriguez, et al., Turning the Adhesion of Layer-by-Layer Films to the Physiochemical Properties of Inner Limiting Membranes using Navo Particles.
Celimar Valentine-Rodriguez, et al., Quantitative Analysis of Human Internal Limiting Membrane Extraction from Patients with Maclar Holes, Jul. 2, 2010.
M. Hess et al., Terminology of Polymers Containing Ionizable or Ionic Groups and of Polymers Containing Ions 2006.
Celimar Valentine-Rodriguez, et al., Surface Modification of Vitreorectinal Surgical Instruments with Layer-by-Layer Films. 2011.
Nevdeck, Gerold W. et al., Fabrication of a Silicon Micro-Scalpel with a Nanometer Cutting Edge, May 1, 2003.
Development of Microelectromechanical Systems (MEMS) Forceps for Intraocular Surgery, R.B. Bhisitkul, CG Keller, BR. J Ophthalmol 2005; 89:1586-1588.
Nikkhah M, et al. (2012). Engineering microsale topographies to control the cell-substrate interface. Biomaterials, 33, 5230-5246.
Hubschman, et al. (2010). "The Microhand": a new concept of micro-forceps for ocular robotic surgery. Eye, 24, 364-367.
Aimi, M. F., Rao, M. P., Macdonald, N. C., Zuruzi, A. S., & Bothman, D. P. (n.d.). High-aspect-ratio bulk micromachining of titanium. Nature Materials, 3, 103-105. Retrieved from www.nature.com/naturematerials.
EFAB Technology for Medical Devices: An Introduction Pamphlet. A Wafer-Based, 3-D Metal Micro-Manufacturing Technology for Ultraminiaturized Medical Devices Pamphlet.
Heriban, D., Gauthier, M., Regnier, S., Chaillet, N., Lutz, P. Automatic pick-and-place of 40 microns objects using a robotic platform. H. Van Brussel, E. Briksmeier, H. Spaan, T. Burke. 9t International Conference of the European Society for Pre-cision Engineering and Nanotechnology, EUSPEN'09., Jun. 2009, San Sebastian, Spain. II, pp. 515-518, 2009. <hal-00404444>.
Research: Micro-Scale Surgical Tools_LIBNA.
Lieberman, D. M., M.D. ( Dec. 1976). Suturing Forceps for Microsurgery. American Journal of Ophthalmology, 82(6), 939-940.
Aoki, I, Takahashi, T., Mihara, S., Yamagata, Y., Higuchi, T., Trial Production of Medical Micro-Tool by Metal Deformation Processes Using Moulds, 344-349.
Dargahi, J., Parameswaran, M., & Payandeh, S. (n.d.). (Oct. 1998). A Micromachined Pizoelectric Tactile Sensor for use in Endoscopic Graspers. Intl. Conference on Intelligent Robots and Systems, 1503-1508.
Bustillo, J. L, M.D. (1975). Corneal Forceps. American Journal of Ophthalmology, 80(1), 152-153.

\* cited by examiner

SURGICAL INSTRUMENT HAVING A SURFACE TEXTURE

CROSS REFERENCE TO RELATED APPLICATIONS

This application claims the benefit of U.S. Provisional Application No. 62/409,660, filed Oct. 18, 2016, and claims the benefit of U.S. Provisional Application No. 62/517,504, filed Jun. 9, 2017, the entire contents of both being incorporated herein by reference.

TECHNICAL FIELD

The present disclosure relates surgical instruments and, in particular, to surgical instruments having a textured surface for improved grasping a membrane so as to avoid damage to underlying tissues.

SUMMARY

According to one aspect, the disclosure describes a surgical instrument that includes an engaging member that engages a tissue of a body. The engaging member may include a surface. The surgical instrument may also include a first plurality of traces formed in the surface in a first direction and a second plurality of traces formed in the surface in a second direction different from the first direction. A first spacing between adjacent traces of the first plurality of traces may be within a range of approximately 5.5 μm to 15 μm. A second spacing between adjacent traces of the second plurality of traces may be within a range of approximately 5.5 μm to 15 μm. The first plurality of traces and the second plurality of traces may define an array of microposts. The microposts of the array of microposts may have a height within a range of 3 μm to 10 μm.

Another aspect of the disclosure encompasses a method of forming a textured surface on a surgical instrument. The method may include forming a first plurality of traces along a surface of an engagement member of the surgical instrument in a first direction and forming a second plurality of traces on the surface in a second direction different than the first direction. A first spacing between adjacent traces of the first plurality of traces may be within a range of approximately 5.5 μm to 15 μm. A second spacing between adjacent traces of the second plurality of traces may be within a range of approximately 5.5 μm to 15 μm. The first plurality of traces and the second plurality of traces may define an array of microposts. The microposts may have a height within a range of 3 μm to 10 μm.

The various aspects may include one or more of the following features. One or more of the microposts of the array of microposts may be inclined at an angle within a range of 20° to 55° relative to the surface of the engaging member. One or more of the microposts of the array of microposts may be inclined at an angle within a range of 30° to 45°. The microposts of the array of microposts may have a height within a range of 3.5 μm to 7 μm. A width of the traces of the first plurality of traces and the second plurality of traces may be approximately 2 μm. The microposts may be tapered. The engaging member may be a forceps jaw, and the surface may be a distal surface of the forceps jaw. The engaging member may include a tip defining an edge. The first plurality of traces may be substantially parallel to the edge, and the second plurality of traces may be substantially perpendicular to the edge. The engaging member may include a tip defining an edge, and the first plurality of traces and the second plurality of traces may be oblique to the edge.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

DETAILED DESCRIPTION

Figure 1:
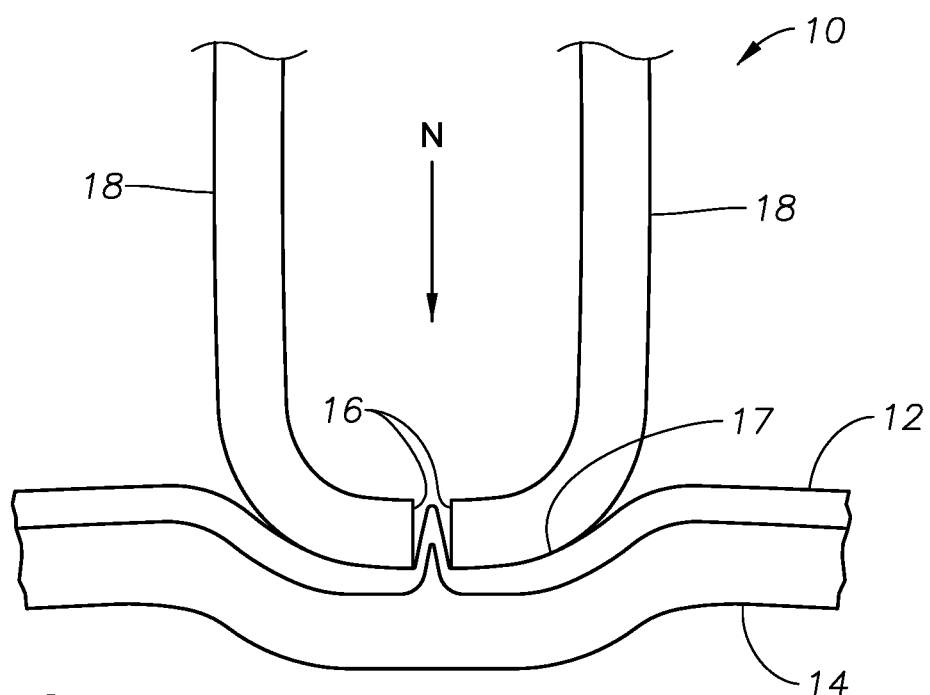
FIG. 1 shows a conventional forceps engaged with an internal limiting membrane that is attached to a retina.

For the purposes of promoting an understanding of the principles of the present disclosure, reference will now be made to the implementations illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one implementation may be combined with the features, components, and/or steps described with respect to other implementations of the present disclosure.

The present description is made in the context of surgical forceps for microsurgical procedures. Particularly, the present description is directed to surgical forceps having a textured surface for atraumatic engagement and peeling of a membrane and, more particularly, to surgical forceps having a textured surface for use in ophthalmic surgical procedures. However, the scope of the disclosure is not so limited. Rather, the surface texture described herein may be applied to other types of surgical instruments for use in medical areas both in and outside of ophthalmology. Consequently, the present description made in the context of ophthalmic surgical forceps is provided merely as an example and is not intended to be limiting.

FIG. 1 illustrates a conventional forceps 10 in the course of attempting to remove an internal limiting membrane (ILM) 12, which is a membrane formed on the retina 14 and separating the retina from the vitreous humor in an eye. Traditionally, to remove the ILM, a user, such as a surgeon, would press a forceps 10 against the retina 14, i.e., a force normal to the surface of the retina 14, and then apply a closing force to close the forceps in order to trap a portion of the ILM 12 between the tips 16 of the forceps jaws 18. The normal force applied to the retina 14 causes an indentation 17 in the retina, as shown in FIG. 1. The normal force applied to the retina 14 via the forceps 10 generates a friction force between the forceps 10 and the ILM 12. An increase in the normal force increases the associated frictional force. The friction force is generated in order to form a flap in the ILM 12. The flap is then used to remove the ILM 12 via use of the forceps 10. Too large of a normal force imposed by the forceps 10 could cause unintended injury to the retina 14. Also, if the normal force was too large or the distance between the forceps tips 16 were too great, closure of the forceps jaws 18 risked trapping a portion of the underlying retina between the forceps tips 16. Pinching of the retina 14 also risks damage to the retina 14. This damage would be further exacerbated by pulling of the forceps in order to begin peeling the ILM 12. With a portion of the retina 14, too, grasped by the forceps 10, the peeling action could further injure the retina 14 and potentially create a retinal tear.

Figure 2:
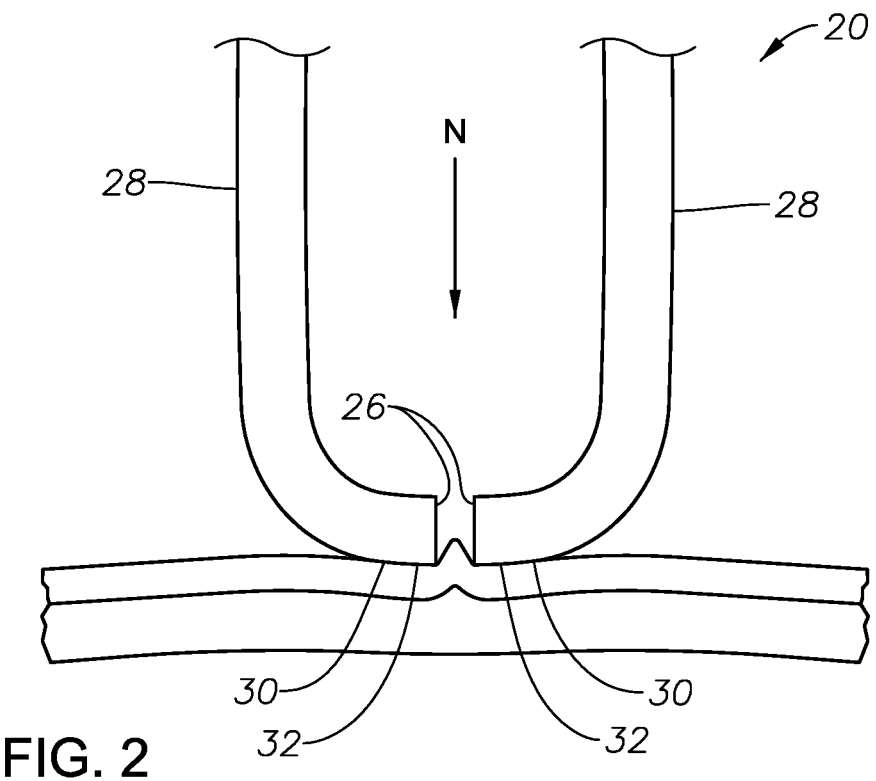
FIG. 2 shows an example forceps having a textured surface formed on a distal end of the forceps jaws engaged with an internal limiting membrane.

FIG. 2 illustrates an example forceps 20 within the scope of the present disclosure. The forceps 20 includes a textured surface 30 formed of a plurality of surface features, shown in FIGS. 3 and 4, for example. In the illustrated example, the textured surface 30 is formed into and along a distal surface 32 of the forceps jaws 28. The textured surface 30 increases friction between the forceps 10 and the ILM 12 by providing a higher coefficient of friction. With a higher coefficient of friction, the normal force needed to engage the ILM 12 is reduced. As a result of the reduced normal force, an indentation formed in the retina 14 and ILM 12 is reduced. The reduced normal force imparted by the jaws 28 of the forceps 20 reduces the risk of injury to the retina 14. With a lower normal force applied to the ILM 12 and the corresponding reduction in indentation formed in the retina 14 and ILM 12, the risk of trapping a portion of the retina 14 between tips 26 of the forceps jaws 28 is also reduced, which, in turn, also reduces the risk of injury to the retina 14 both when the forceps jaws 28 are closed and peeling of the ILM 12 is commenced.

Figure 3:
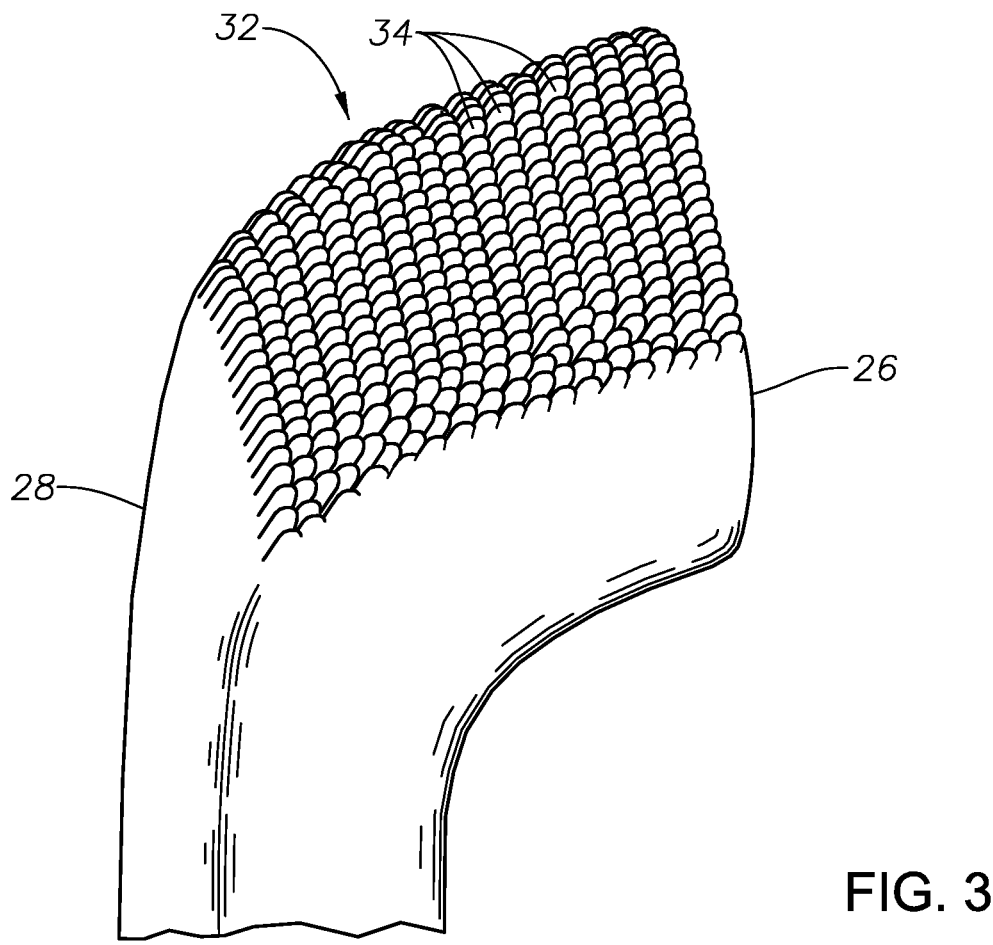
FIG. 3 shows a distal end of a forceps jaw of the forceps shown in FIG. 2.
Figure 4:
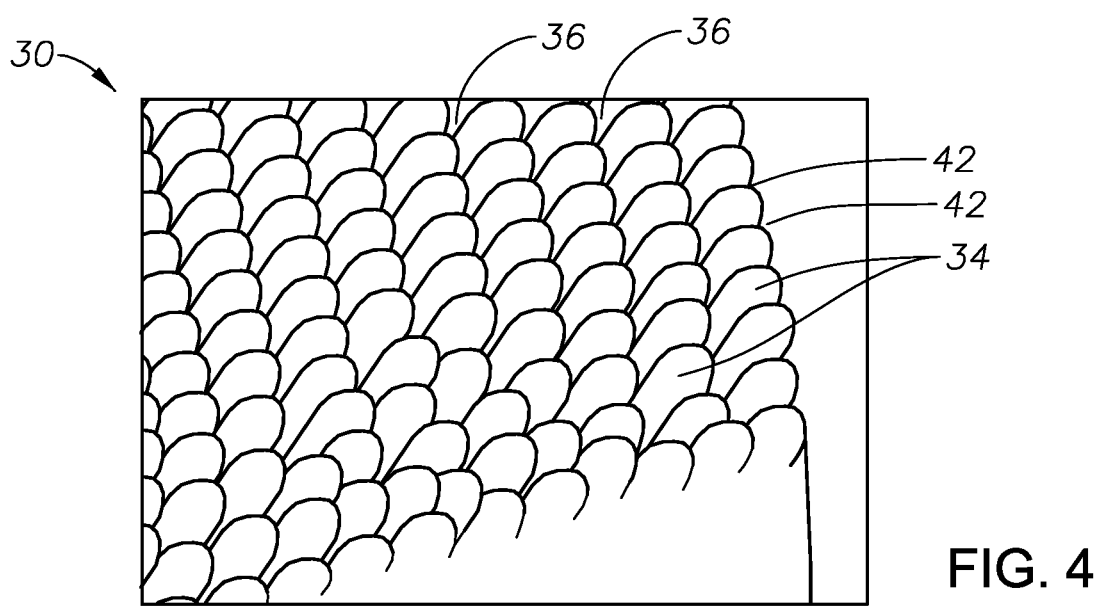
FIG. 4 is a detail view of a textured surface formed on the distal end of the forceps jaw shown in FIG. 3.

FIG. 4 is a magnified image of the textured surface 30 shown in FIG. 3. The textured surface 30 includes a plurality of surface features or microposts 34. In the illustrated example, the microposts 34 are formed by application of laser energy to the distal surface 32 of the forceps jaws 28. The textured surface 30 works to increase a coefficient of friction between the forceps 20 and the ILM 12. As a result, a size of the normal force needed to grasp the ILM 12 with the forceps 20 is decreased. Therefore, a user, such as a surgeon, is able to apply a lower normal force to the ILM 12 and retina 14 with the forceps 20 in order to engage the ILM 12. Consequently, the risk of injury to the retina 14 is decreased.

Figure 5:
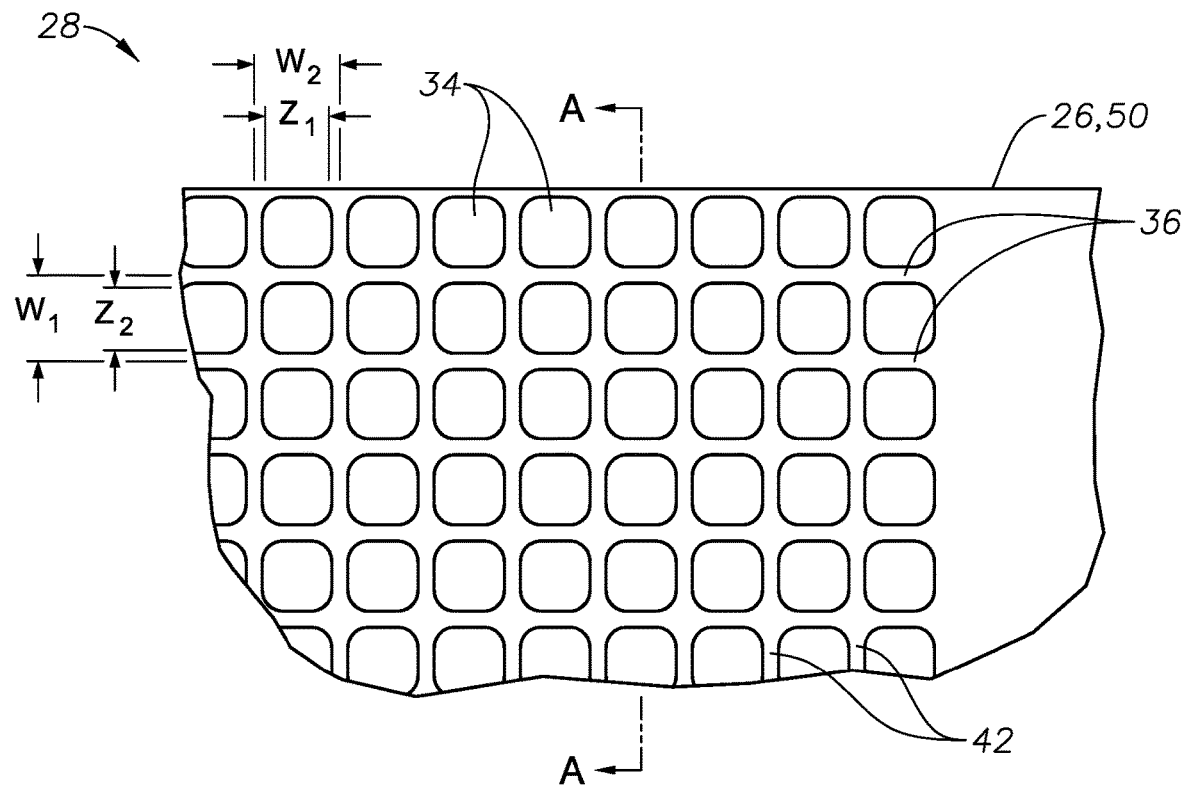
FIG. 5 shows a spacing distance between adjacent traces forming the textured surface.

FIG. 5 is a view of the textured surface 30 taken normal to the microposts 34 and shows an edge 50 defined by the tip 26 of the forceps jaw 28. FIG. 5 shows a plurality of laser cuts or traces 36 and 42 formed in the distal surface 32. The plurality of laser traces 36 and 42 define an array of the microposts 34. In some implementations, a laser beam used to form the laser traces 42 may be normal or substantially normal to the distal surface 32 of the forceps jaws 28. In this context, the term "substantially normal" may account for variations of an incident laser beam from being perpendicular to the distal surface 32 due to, for example, variations due to a fixed position of the laser source and a curvature of the distal surface 32, variations in the distal surface 32, misalignment of the laser source, and variations in a targeting and directional system used to control movement of the laser beam when forming the laser traces 42.

Figure 6:
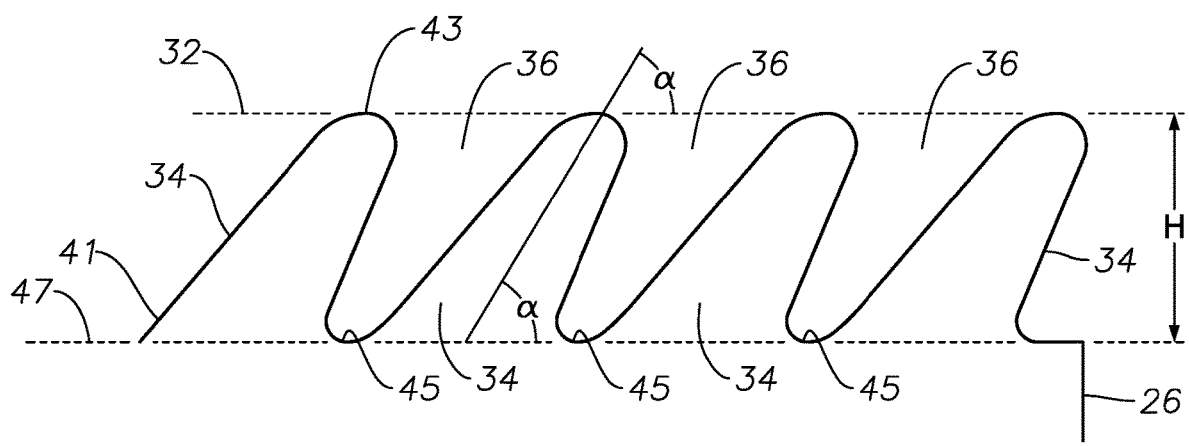
FIG. 6 is a cross-sectional view of a textured surface showing microposts of the textured surface.

FIG. 6 shows a cross-sectional view of the textured surface 30 taken along line AA and showing the microposts 34 in profile. The distal surface 32 into which the textured surface 30 is formed is illustrated as a dotted line. A laser beam used to form the traces 36 may be incident to the distal surface 32 at an angle $\alpha$. In some implementations, a femtosecond or picosecond laser may be used. Further, in some implementations, the laser may be a solid-state laser. The angle $\alpha$ is measured relative to the distal surface 32. In some implementations, the angle $\alpha$ may be within a range of 10° to 90°, where 90° would be perpendicular to the distal surface 32. In some implementations, the angle $\alpha$ may be within a range of 20° to 70°; 20° to 55°; 30° to 60°; 40° to 50°; 20° to 50°; or 30° to 45°. As shown in FIG. 6, in addition to the microposts 34 being illustrated at an angle as a result of the angle $\alpha$ of the traces 36, the illustrated microposts 34 also include a tapered profile. Thus, a cross sectional size of the microposts 34 is larger at towards a base 41, i.e., at a location where the microposts 34 are attached to the forceps jaws 28, and decreases towards an end 43. Although FIG. 6 shows all of the microposts 34 as being incident at the same angle, the scope of the disclosure is not so limited. Rather, in other implementations, an angle $\alpha$ of one or more of the microposts 34 may vary from one or more other microposts 34.

As the example shown in FIG. 6 illustrates, the angle $\alpha$ results in the microposts 34 inclining towards the tip 26. However, the scope of the disclosure is not so limited. Thus, in other implementations, the microposts 34 may be inclined in any direction relative to the tip 26. Further, in other implementations, the one or more of the microposts 34 may be included in a direction different from one or more other microposts 34.

A height H of the microposts 34, measured from a trough 45 of the traces 36 and measured perpendicularly from the effective surface 47 defined by a surface passing through the troughs 45. In some implementations, the height H may be 3 µm to 10 µm. In other implementations, the height H may be 3.5 µm to 10 µm. In other implementations, the height H may be 3.0 to 7 µm; 3.5 µm to 7 µm; or 5 µm to 7 µm. In still other implementations, the height H of the microposts 34 may be smaller than 3 µm or larger than 10 µm. Further, the heights H of the microposts 34 may vary across the textured surface 30.

Figure 11:
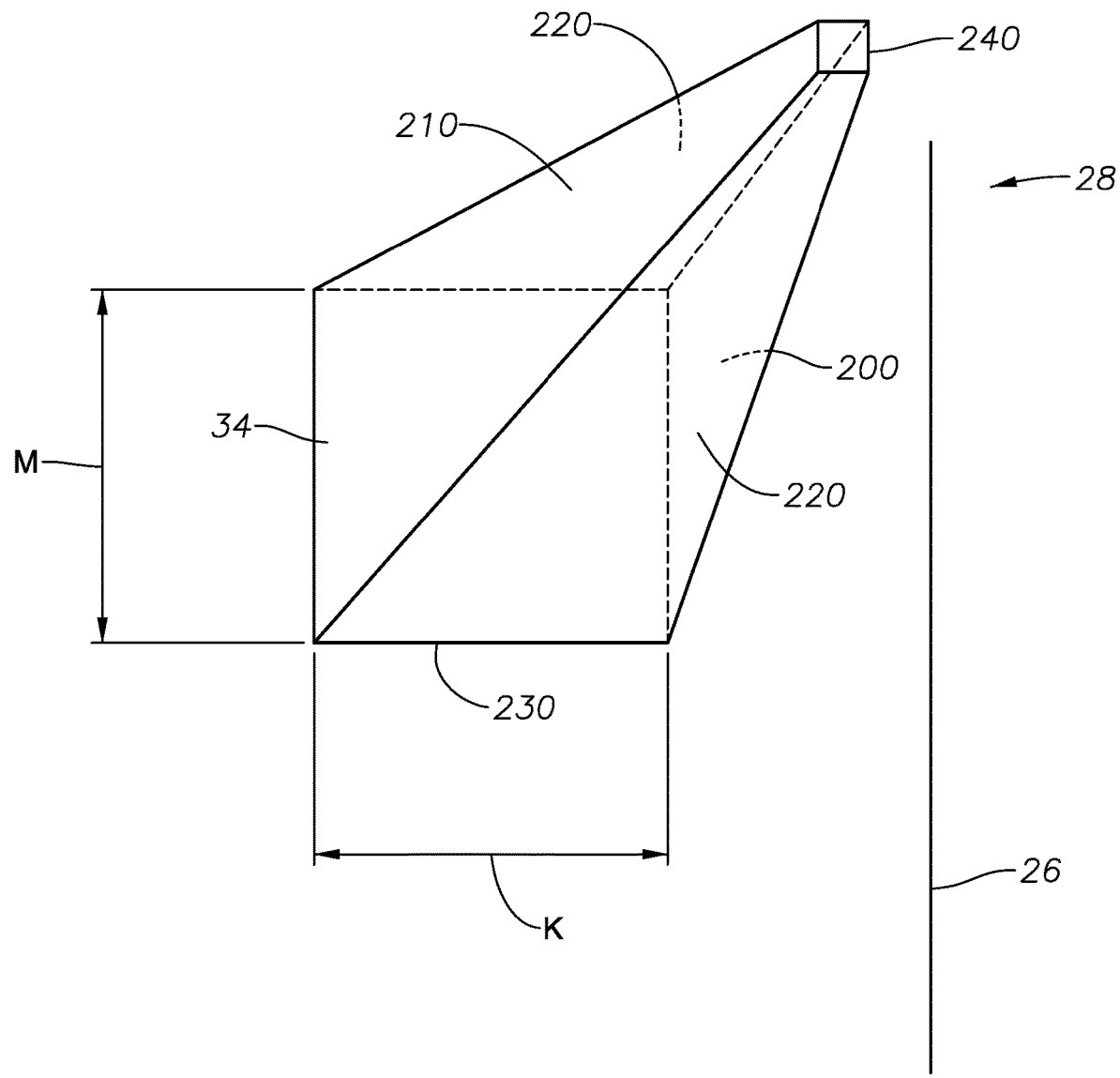
FIG. 11 shows a detail view of a pyramidal micropost disposed on a textured surface of a distal end of a forceps.

In some implementations, the microposts 34 have a four-sided pyramidal shape, as shown, for example, in FIG. 11. FIG. 11 shows the micropost 34 formed on a distal textured surface of forceps jaw 28 proximate to the tip 26. While FIG. 11 shows a single pyramidal micropost 34 for clarity purposes, it is to be understood that a plurality of the pyramidal microposts 34 would be formed on the distal textured surface of the forceps jaw 28.

As illustrated, the pyramidal microposts 34 include four walls that include a leading wall 200, a trailing wall 210, and two side walls 220. The example of FIG. 11 shows an obliquely formed pyramidal micropost 34. In this example, the leading wall 200 is oriented towards the tip 26 of the forceps jaw 28 with the trailing side 210 oriented away from the tip 26 of the forceps jaw 28. The walls 200, 210, and 220 taper from a base 230 to a point 240. The pyramidal microposts 34 may be formed at an oblique angle, as illustrated, for example in FIG. 6, or at a non-oblique angle, as illustrated, for example, in FIGS. 9 and 10. In some instances, the sides of the pyramidal microposts 34 (and, hence, the microposts 34 themselves) are formed as a result of removal of material of the forceps jaw 28 due to ablation during laser forming. In other instances, the wall of the pyramidal microposts 34 may be formed by grinding, etching, or other type of applicable forming method.

The walls 200, 210, and 220 of the pyramidal microposts 34 are disposed at an angle relative to a plane defined by the base 230. In some instances, a length K of the microposts 34 at the base 230 may be within a range of 7 μm and 13 μm. A width M of the microposts 34 may be within the range of 7 μm and 13 μm. In some instances, the length K of one or more of the microposts 34 may be larger than the width M. In other instances, the length K of one or more of the microposts 34 may be smaller than the width M. In still other instances, the length K of one or more of the microposts 34 may be the same as the width M. In some implementations, a height of H (as shown oriented in FIG. 6) may be within the range of 3 μm to 7 μm. The point 240 may have a thickness (as measured in a cross-section of the point 240 defined by a plane parallel to a plane defined by the base 230) in a range of 1.0 μm to 0.5 μm. The point 240 may have a cross-sectional shape (taken along a plane parallel with the base 230 of the micropost 34) that generally corresponds to the shape of the pyramidal micropost 34 at its base 230. Thus, the thickness of the point 240 may be the dimension K or M measured at the point 240. As a practical matter, on the scale contemplated by the present disclosure, the dimensions K and M of the point 240 may not be clearly distinguishable in some implementations. Thus, the thickness of the point 230 may be a largest dimension of the point 230.

Although, pyramidal microposts are illustrated, the scope of the disclosure is not so limited. Rather, in other implementations, the microposts may have a cylindrical shape having a constant cross-section along an entire length of the microposts. Further, in other implementations, a cross-sectional shape of the microposts (taken along a plane parallel with the base of the micropost) may be circular, polygonal, or rectangular, square, or any other desired shape.

It is believe that, when microposts 34 of the present disclosure, particularly in the pyramidal form, the points 240 of the microposts 34 penetrate a membrane, such as the ILM, to aid in removal thereof.

Referring again to FIG. 5, a cross-sectional view of the textured surface taken near the bases 41 of the microposts 34 is illustrated. A width of the laser traces 36 and 42 may be within a range of approximately 2 μm to 30 μm. In some implementations, the width of the laser cuts 36 and 42 may be within a range of 2 μm to 10 μm. In still other implementations, a width of one or more of the laser cuts 36 and 42 may vary from one or more other laser cuts 36 and 42. Thus, in some implementations, a width of one or more laser cuts 36 may be larger or smaller than a width of one or more other laser cuts 36. Similarly, a width of one or more laser cuts 42 may be larger or smaller than a width of one or more other laser cuts 42.

As shown in FIG. 5, a width W1 defines a distance between adjacent traces 36, and a width W2 defines a distance between adjacent traces 42. In some implementations, the widths W1 and W2 may be within a range of 2 μm to 15 μm or within the range of 2 μm to 10 μm. In other implementations, the widths W1 and W2 may be within a range of 2 μm to 7 μm. In other implementations, the widths W1 and W2 may be within a range of 2 μm to 5 μm. In some implementations, the widths W1 and W2 may be different from one another. That is, in some instances, the width W1 of the microposts 34 may be larger or smaller than the width W2. Additionally, cross-sectional sizes of the microposts 34 may vary along the textured surface 30. Thus, in some instances, one or more of the microposts 34 may have a width W1 that is the same as the width W2, while one or more other microposts 34 may have a width W1 that is different from the width W2. Thus, the sizes of the microposts 34 may vary along the textured surface 30.

Near the bases 41 of the microposts 34, the microposts 34 may have cross-sectional dimensions of a Z1 and Z2. The dimensions Z1 and Z2 may substantially correspond to width W1 and a width W2 but be reduced as a result of a width of the laser trace itself. Thus, in some implementations, a size of the dimensions Z1 and/or Z2 may be within a range of 3 μm to 10 μm; 4 μm to 9 μm; or 5 μm to 8 μm. These ranges are provided only as example. Thus, in other implementations, dimensions Z1 and Z2 may be smaller than 3 μm or larger than 10 μm. The size of dimensions Z1 and Z2 may be selected to be any desired size.

FIG. 5 shows an orthogonal grid pattern formed by the laser traces 36 and 42. As shown in FIG. 5, the traces 36 are parallel or may be substantially parallel to the edge 50. The traces 36 may be described as substantially parallel to the edge 50 due, for example, to small variations in orientation of the traces 36 or the edge 50 due to variations in manufacturing or minor misalignments that may result during manufacturing. For example, in some instances, the laser used to form the laser traces 36 may be misaligned with the forceps 20 such that the traces 36 may form slight angle with the edge 50 although a parallel orientation was intended. Also, formation of the tips 26 may result in the tips 26 being slightly out of parallel with the resulting traces 26. Thus, while a parallel relationship between the edge 20 and the traces 36 may be intended, variations in manufacturing may result in a slight deviation between the orientation of the edge 30 and the traces 36.

Figure 7:
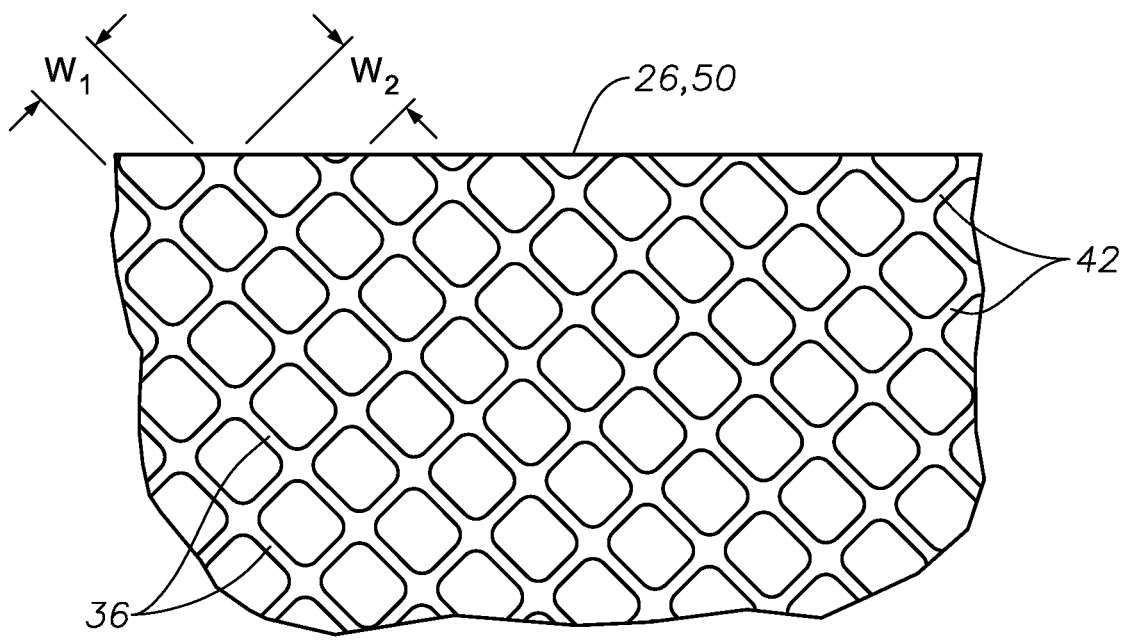
FIGS. 7 and 8 show example textured surface having different surface patterns.
Figure 8:
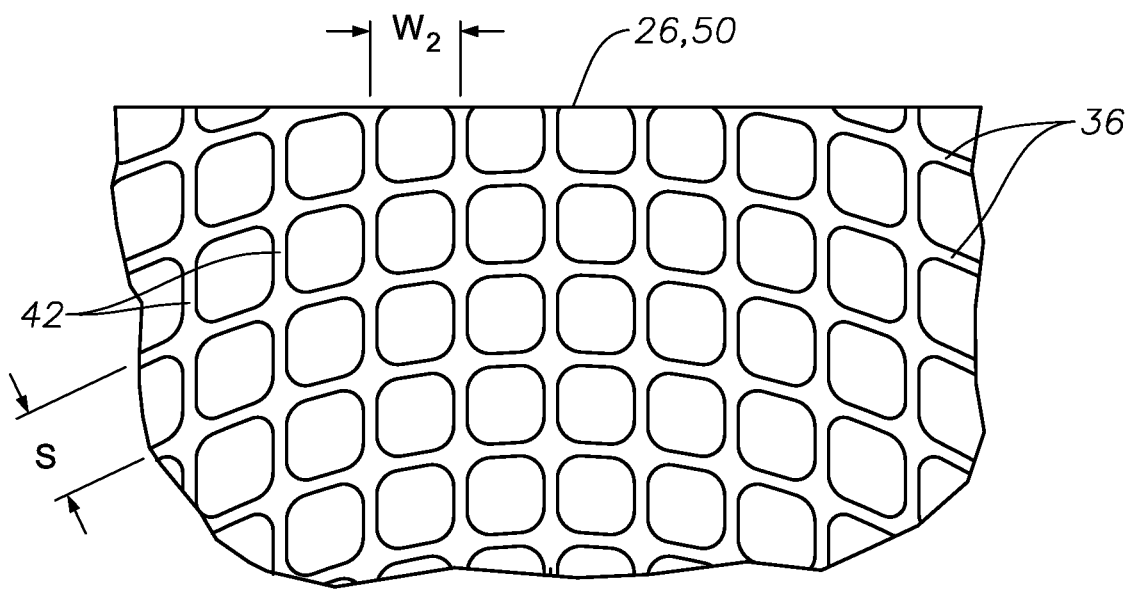

However, the scope of the disclosure is not so limited. Rather, any pattern may be formed in the distal surface 32 of the forceps jaws 28. FIGS. 7-8 show other example patterns of microposts 34 that may be formed on the distal surface 32 of the forceps jaws 28. FIG. 7 shows a pattern in which the laser traces 36 and 42 are oblique to the edge 50 formed by the tips 26. Similar to the example shown in FIG. 5 and described above, the laser traces 36 and 42 form microposts 34 having a width W1 and a width W2. In some instances, the traces 36 and 42 may be selected such that the widths W1 and W2 are the same. In other instances, the widths W1 and W2 may be different. Still further, one or more of the widths W1 and W2 may vary along the textured surface 30 to produce microposts 34 of varying sizes.

FIG. 8 shows another example pattern formed by laser traces 36 and 42. In this example, the traces 36 are circular or scalloped shaped whereas the traces 42 are straight. In some implementations, spacing S between the traces 36 may be equal. In other instances, the spacing S may vary over the textured surface 30. Similarly, in some implementations, width W2 between the traces 42 may be equal. In other implementations, the textured surface 30 may include different widths W2. While FIGS. 7 and 8 show two additional examples of patterns of microposts 34 that may be formed on the textured surface 30, any other desired pattern is also included within the scope of the present disclosure.

Figure 9:
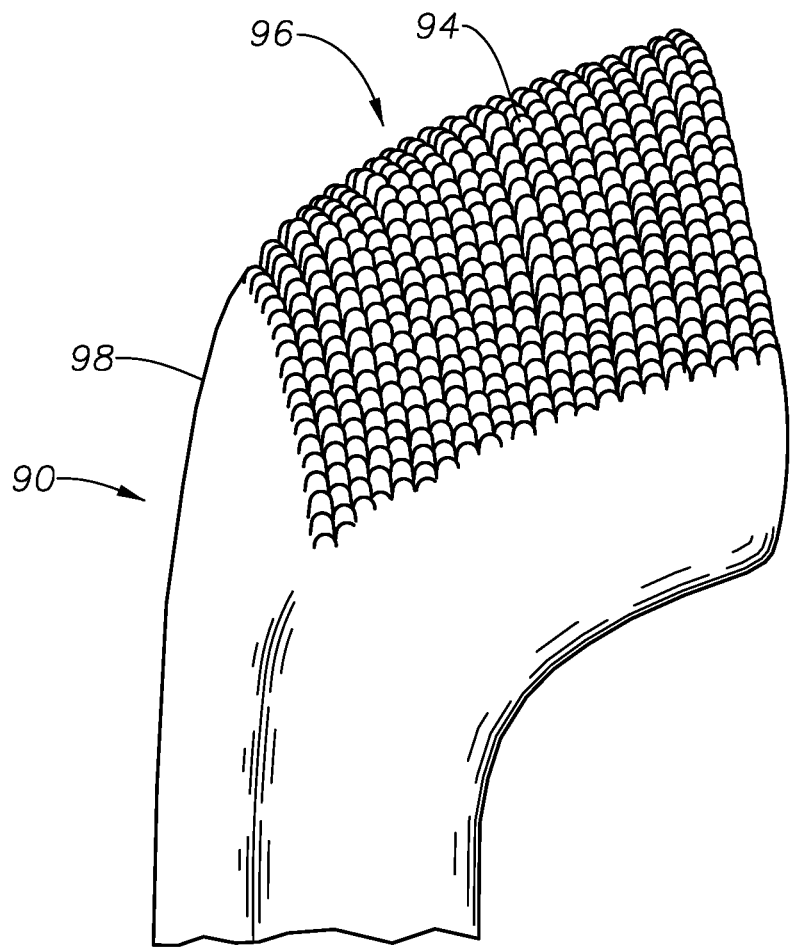
FIG. 9 shows another example forceps jaw having a textured surface formed thereon at a distal end thereof.
Figure 10:
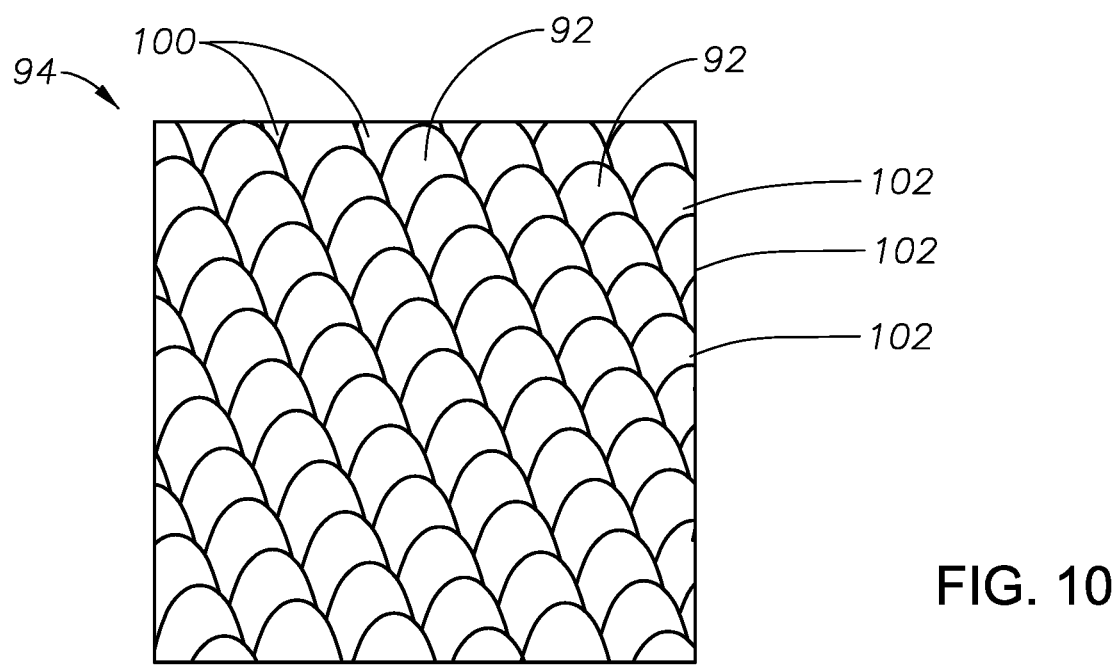
FIG. 10 is a detail view of the surface texture shown in FIG. 9.

FIGS. 9 and 10 illustrate another example forceps 90. The forceps 90 may be similar to the forceps 20, described above. However microposts 92 of a textured surface 94 formed on the distal surface 96 of forceps jaws 98 do not include an inclination. That is, the angle α is 90°. Also similar to the example forceps 20 described above, the distances W1 and W2 between respective adjacent laser traces 100 and 102 and the sizes Z1 and Z2 and height H of the microposts 92 may have the same ranges described above.

Although the present disclosure is made in context of forceps, the scope of the disclosure is not so limited. Rather, a textured surface of a type described herein may be applied other types of instruments, such as, for example, scissors, scrapers, spatulas, etc., and may be used. Further, instruments having a textured surface as described herein may be used in other medical or technological areas.

While the various examples described above are described in the context of forming surface features using laser energy. However, the scope of the disclosure is not so limited. Rather, other processes may be used to form the microposts and are within the scope of the present disclosure. For example, chemical etching may also be used to for the microposts by chemically removing material. The material removed for a surface to define the microposts may be in the form of a plurality of valley or grooves (referred to collectively as "traces"). Thus, while laser traces are described in the context of traces formed by laser energy, the general term "trace" is used to describe a grooves, cuts, or valleys formed in a surface of an instrument, for example, to define a surface texture and surface features thereof.

In other implementations, the traces may be formed via photolithography. For example, in some instances, a desired pattern may be masked on a portion of the surgical instrument, such as with the use of a photoresist material. The photoresist material may be positive photoresist or a negative photoresist. The photoresist material may be exposed to radiation (e.g., ultraviolet or other frequency of radiation) to define the pattern to be etched. A chemical solution may be applied to the masked area to remove a portion of the photoresist material so that the desired pattern is defined. The masked surface may be washed, and an etchant may be applied to the portion of the surgical instrument having an exposed surface defined by the pattern (i.e., the area on which the photoresist is not present) in order to etch the surface of the surgical material and form the desired topography, e.g., traces.

In some implementations, surgical instruments within the scope of this disclosure may be formed of metal in whole or in part, such as, for example, steel (e.g., stainless steel), titanium, or other metal. In other implementations, the instruments may be formed from a polymer in whole or in part. For example, the instruments may be a polymer tip instrument in which a tip portion of the instrument that is made to come into contact with tissue is formed of a polymer. In other instances, the instruments may be formed, at least in part, of glass. A texture of a type described herein may be formed on a surface of the instruments formed from a polymer by, for example, a chemical etching (e.g., with the use of a photoresist material), laser energy, grinding, molding, or other method.

Persons of ordinary skill in the art will appreciate that the implementations encompassed by the present disclosure are not limited to the particular exemplary implementations described above. In that regard, although illustrative implementations have been shown and described, a wide range of modification, change, combination, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A surgical forceps comprising:
   a forceps jaw that is configured to engage a tissue of a body, the forceps jaw comprising a distal-most surface;
   a first pattern of traces formed in the distal-most surface in a first direction, a first spacing between adjacent traces of the first pattern of traces being within a range of approximately 5.5 μm to 15 μm; and
   a second pattern of traces formed in the distal-most surface in a second direction different from the first direction, a second spacing between adjacent traces of the second pattern of traces being within a range of approximately 5.5 μm to 15 μm, the first pattern of traces and the second pattern of traces defining an array of microposts, the microposts of the array of microposts have a height within a range of 3 μm to 10 μm;
   wherein the forceps jaw comprises a tip defining an edge, wherein the first pattern of traces is substantially parallel to the edge, and wherein the second pattern of traces is substantially perpendicular to the edge;
   wherein the first pattern of traces and the second pattern of traces are laser cuts, wherein a laser beam used to cut the traces is incident to the distal-most surface at an angle such that one or more of the microposts of the array of microposts are tapered and inclined at an angle within a range of 20° to 55° relative to the distal-most surface of the forceps jaw.

2. The surgical forceps of claim 1, wherein one or more of the microposts of the array of microposts are inclined at an angle within a range of 30° to 45°.

3. The surgical forceps of claim 1, wherein the microposts of the array of microposts have a height within a range of 3.5 μm to 7 μm.

4. The surgical forceps of claim 1, wherein a width of the traces of the first pattern of traces and the second pattern of traces is approximately 2 μm.

5. The surgical forceps of claim 1, wherein the forceps jaw comprises a tip defining an edge, wherein the first pattern of traces and the second pattern of traces are oblique to the edge.

* * * * *